US00PP31313P2

(12) United States Plant Patent
Smit

(10) Patent No.: US PP31,313 P2
(45) Date of Patent: Dec. 31, 2019

(54) ***PEPEROMIA* PLANT NAMED 'EC-PEPE-1806'**

(50) Latin Name: *Peperomia obtusifolia*
Varietal Denomination: EC-PEPE-1806

(71) Applicant: Obed Jacob Smit, Sappemeer (NL)

(72) Inventor: Obed Jacob Smit, Sappemeer (NL)

(73) Assignee: Eden Collection B.V., Sappemeer (NL)

( * ) Notice: Subject to any disclaimer, the term of this patent is extended or adjusted under 35 U.S.C. 154(b) by 0 days.

(21) Appl. No.: 16/350,745

(22) Filed: Dec. 31, 2018

(51) Int. Cl.
*A01H 5/12* (2018.01)

(52) U.S. Cl.
USPC ..... Plt./373

(58) Field of Classification Search
USPC ..... Plt./373
CPC ... A01H 6/00; A01H 5/00; A01H 5/02; A01H 5/12
See application file for complete search history.

*Primary Examiner* — Keith O. Robinson

(57) ABSTRACT

A new cultivar of *Peperomia* plant named 'EC-PEPE-1806' that is characterized by glossy broad obovate shaped green leaves with clearly visible veins and red stems with large internodes.

1 Drawing Sheet

Botanical classification: *Peperomia obtusifolia.*
Variety denomination: 'EC-PEPE-1806'.

BACKGROUND OF THE INVENTION

The present invention relates to a new and distinct cultivar of *Peperomia* plant botanically known as *Peperomia obtusifolia* and hereinafter referred to by the cultivar name 'EC-PEPE-1806'.

'EC-PEPE-1806' originated from the crossing of the female or seed parent, an unnamed *Peperomia obtusifolia* cultivar and the male or pollen parent, an unnamed *Peperomia obtusifolia* cultivar. The crossing was conducted in 2015 in Sappemeer, Netherlands. The resulting seeds were subsequently planted and grown. The cultivar 'EC-PEPE-1806' was selected by the inventor in 2017 in a controlled environment as a single plant within the progeny of the stated cross in a cultivated area of Sappemeer, Netherlands.

Asexual reproduction of the new cultivar 'EC-PEPE-1806' first occurred by tip cuttings in 2017 in Sappemeer, Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Peperomia* cultivar 'EC-PEPE-1806'. These traits in combination distinguish 'EC-PEPE-1806' as a new and distinct cultivar apart from other existing varieties of *Peperomia* known by the inventor.

1. *Peperomia* 'EC-PEPE-1806' exhibits glossy broad obovate shaped green leaves with clearly visible veins.
2. *Peperomia* 'EC-PEPE-1806' exhibits red stems with large internodes.

The closest comparison cultivars are *Peperomia* 'Bohemian Bravour' (not patented) and *Peperomia* 'Obtipan Bicolor' (not patented). 'EC-PEPE-1806' is distinguishable from 'Bohemian Bravour' by the following characteristics:

1. *Peperomia* 'EC-PEPE-1806' exhibits glossy broad obovate shaped green leaves with clearly visible veins. In comparison, the leaves of 'Bohemian Bravour' are not glossy and the leaf veins are not clearly visible.
2. *Peperomia* 'EC-PEPE-1806' exhibits red stems. In comparison, the stems of 'Bohemian Bravour' are brown.

'EC-PEPE-1806' is distinguishable from 'Obtipan Bicolor' by the following characteristics:

1. *Peperomia* 'EC-PEPE-1806' exhibits glossy broad obovate shaped green leaves with clearly visible veins. In comparison, the leaves of 'Obtipan Bicolor' are white and green.
2. *Peperomia* 'EC-PEPE-1806' exhibits red stems. In comparison, the stems of 'Obtipan Bicolor' are brown.

'EC-PEPE-1806' is distinguishable from the female parent plant, by the following characteristics:

1. The stems of 'EC-PEPE-1806' are red. In comparison, the stems of the female parent plant are brown.

'EC-PEPE-1806' is distinguishable from the male parent plant by the following characteristics:

1. The leaves of 'EC-PEPE-1806' are glossy green with clearly visible veins. In comparison, the leaves of the male parent plant are not glossy and the leaf veins are not clearly visible.

BRIEF DESCRIPTION OF THE DRAWING

The accompanying photograph illustrates the distinguishing traits of *Peperomia* 'EC-PEPE-1806'. The photograph shows an overall view of a 30 week old plant. The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new *Peperomia* cultivar named 'EC-PEPE-1806'. Data was collected in Sappemeer, Netherlands from 30 week old plants grown in a glass greenhouse in 15 cm. diameter containers. The time of year was Winter and the temperature range was 20-23 degrees Centigrade during the day and 18-20 degrees Centigrade at night. The light level was natural light level. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'EC-PEPE-1806' has not been tested under all possible conditions and phenotypic differences may be observed with variations in environmental, climatic, and cultural conditions, however, without any variance in genotype.

Botanical classification: *Peperomia obtusifolia* 'EC-PEPE-1806'.

Annual or perennial: Perennial.

Parentage: 'EC-PEPE-1806' is a hybrid of the female parent, an unnamed *Peperomia obtusifolia* cultivar and the male parent an unnamed *Peperomia obtusifolia* cultivar.

Plant type: Potted plant.

Growth habit: Broad upright.

Plant shape: Broad Obovate.

Suitable container size: 9 cm. pots or larger.

Plant height to top of foliage plane: Average 23.6 cm.

Plant width: Average 23.2 cm.

Vigor: Moderate to high.

Growth rate: Moderate high.

Low temperature tolerance: 10° Centigrade.

High temperature tolerance: 35° Centigrade.

Propagation: Tip cuttings.

Time to initiate roots: Tip cuttings are placed directly in growing containers.

Crop time: Approximately 25 weeks in Sappemeer, Netherlands.

Root system: Fibrous.

Plant fragrance: None.

Stem:

*Branching habit*.—Main branches grow from base with lateral branches.

*Basal branching*.—Yes.

*Pinching*.—Not required.

*Number of main branches per plant*.—Average 2.

*Number of lateral branches per plant*.—Average 3.

*Main branch dimensions*.—Average 22.5 cm. in length and 0.9 cm. in diameter.

*Internode length*.—4.8 cm.

*Stem appearance*.—Succulent.

*Stem shape*.—Rounded.

*Stem texture*.—Smooth.

*Stem luster*.—Moderately glossy.

*Stem pubescence*.—Absent.

*Stem angle*.—Average 40 degrees from vertical.

*Stem strength*.—Moderately strong.

*Stem color* (*young*).—Between N186C and 200B.

*Stem color* (*mature*).—183A to 183B.

*Internode color*.—146C to 146D, covered with fine dots 183D.

Foliage:

*Leaf arrangement*.—Alternate.

*Compound or single*.—Single.

*Quantity of leaves per lateral branch*.—Average 6.

*Leaf shape*.—Broad obovate.

*Leaf aspect*.—Moderately concave.

*Leaf apex*.—Rounded to undeeply retuse.

*Leaf base*.—Short attenuate.

*Leaf dimensions*.—Average 10.8 cm. in length and 8.6 cm. in width.

*Texture*.—Glabrous, very leathery (both surfaces).

*Leaf luster upper surface*.—Glossy.

*Leaf luster lower surface*.—Moderately glossy.

*Pubescence*.—Absent (both surfaces).

*Leaf margin*.—Entire.

*Leaf lobed*.—Not lobed.

*Leaf rugose*.—Not rugose (both surfaces).

*Venation pattern*.—Pinnate, slightly furrowed.

*Young leaf color* (*upper surface*).—143A.

*Young leaf color* (*lower surface*).—Between 138B and 145A.

*Mature leaf color* (*upper surface*).—Between NN137A and 139A.

*Mature leaf color* (*lower surface*).—Between 144A and 144B.

*Vein color* (*upper surface*).—144B.

*Vein color* (*lower surface*).—144A, main vein fading toward base of leaf 183A to 183B.

Petiole:

*Petiole dimensions*.—Petiole slightly flattened, average 1.8 cm. in length, 0.6 cm. in diameter at widest, 0.45 cm. in diameter at narrowest.

*Petiole texture*.—Glabrous.

*Petiole luster*.—Slightly glossy on both sides.

*Petiole pubescence*.—Absent.

*Petiole strength*.—Moderate.

*Petiole color* (*upper side*).—183B.

*Petiole color* (*lower side*).—183A.

Flower: 'EC-PEPE-1806' has not produced flowers to date.

Fruit and seed: 'EC-PEPE-1806' has not produced fruit or seed to date.

Disease and pest resistance: Disease and pest resistance has not been observed.

The invention claimed is:

1. A new and distinct variety of *Peperomia* plant named 'EC-PEPE-1806' as described and illustrated.

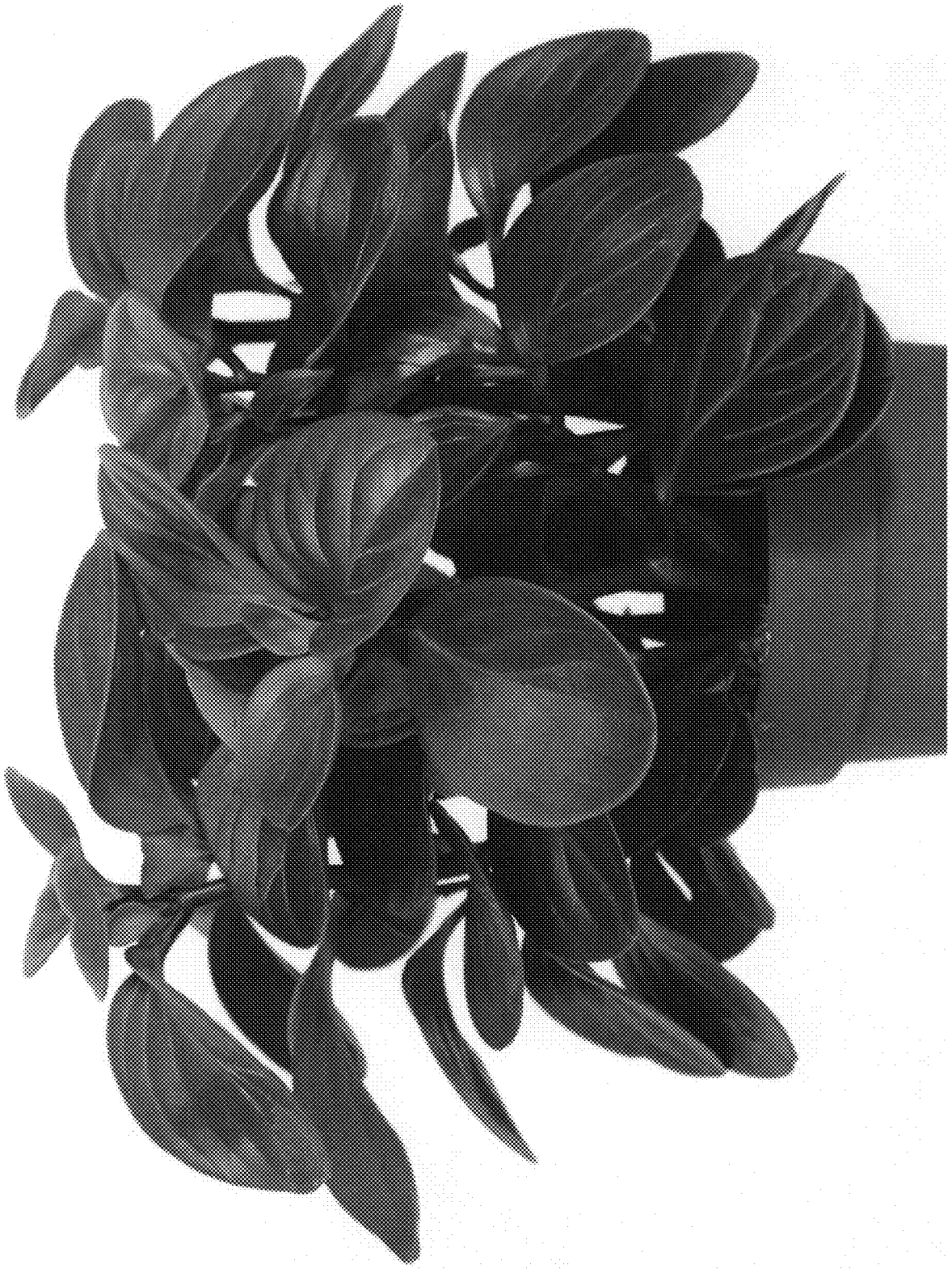

* * * * *